United States Patent [19]

Ott

[11] 4,091,441
[45] May 23, 1978

[54] FULL-SPECTRUM LUMINAIRE

[75] Inventor: John Nash Ott, Sarasota, Fla.

[73] Assignee: John Ott Laboratories, Inc., Sarasota, Fla.

[21] Appl. No.: 848,575

[22] Filed: Nov. 4, 1977

Related U.S. Application Data

[63] Continuation of Ser. No. 700,089, Jun. 28, 1976, abandoned.

[51] Int. Cl.$^2$ .......................... F21S 7/00; H05B 35/00
[52] U.S. Cl. ........................................ 362/1; 362/231; 315/153; 315/314; 315/360
[58] Field of Search .......................................... 362/1, 2

[56] References Cited

U.S. PATENT DOCUMENTS

| | | | |
|---|---|---|---|
| 2,725,461 | 11/1955 | Armour | 362/1 |
| 3,093,319 | 6/1963 | Gamain | 362/1 |
| 3,355,982 | 12/1967 | Rendina | 362/2 X |

Primary Examiner—Alfred E. Smith
Assistant Examiner—Charles F. Roberts
Attorney, Agent, or Firm—Richard E. Hosley

[57] ABSTRACT

An improved full-spectrum luminaire utilizing a plurality of gas discharge lamps at least one of which produces radiant energy primarily in the near-ultraviolet range and another produces radiant energy primarily in the visible range. The spectral energy distribution characteristics of the lamps are chosen so that their combined radiation simulates natural daylight in both the ultraviolet and visible light ranges. The ultraviolet radiation may be switched off manually or automatically.

5 Claims, 6 Drawing Figures

FULL-SPECTRUM LUMINAIRE

This is a continuation of application Ser. No. 700,089, filed June 28, 1976 now abandoned.

BACKGROUND OF THE INVENTION

The present invention relates to luminaires having gas discharge type light sources such as fluorescent lamps and, more particularly, to an improved luminaire whose light has a spectral composition similar to natural daylight in both ultraviolet (UV) and visible light wavelength bands.

It is now recognized that natural daylight produced by the sun is a very important environmental element and that growth responses and photo-biological processes in plants, animals, and human beings are probably the result of adaptation to the intensity, periodicity and spectral composition of radiation from the sun that reaches the earth. Modern civilization has brought about drastic changes in this light environment. A major cause of this change is the widespread use of artificial light sources which grossly distort the natural balance of the various wavelengths found in sunlight energy.

Artificial light sources as fluorescent lamps used for general illumination are usually deficient in near (long wave) ultraviolet range of wavelengths (320 to 380 nanometers). Such radiation, which is found in natural daylight, is believed to be important in maintaining normal photo-biological responses. To remedy this defect fluorescent lamps of the so-called full-spectrum type have been developed utilizing, in a single envelope, a combination of phosphors which produce ultraviolet as well as visible light in approximately the same proportion as found in natural daylight. Such a lamp is disclosed, for example, in U.S. Pat. No. 3,670,193. While such full-spectrum lamps are a great improvement in providing artificial illumination closer to natural daylight, there are cost disadvantages connected with their use for some applications.

One problem connected with the use of full-spectrum fluorescent lamps arises from the fact that the phosphors used to produce the UV part of the radiation degrade more rapidly than those which produce the visible light. This requires more frequent replacement of the full-spectrum lamps than needed for conventional fluorescent lamps, and this increases operating costs.

Another problem might arise if full-spectrum lamps with optimum UV output for short periods are burned continuously as in factories and offices where employees work on the night shift. This could result in UV overexposure unless the lamps are turned off periodically. This would require substitution of other types of lighting resulting in duplication of lighting fixtures.

Accordingly, it is an object of this invention to provide an improved full-spectrum luminaire arrangement which substantially reduces lamp cost.

Another object of the invention is to provide a full-spectrum luminaire in which the UV part of the radiation can be conveniently switched off while permitting continued use of the luminaire for general illumination.

A still further object of the invention is to provide a full-spectrum luminaire in which the UV part of the radiation may be switched on and off at timed intervals correlated with the time of day to simulate the periodicity of the UV part of the radiation in natural daylight.

Further objects and advantages of the invention will become apparent as the following description proceeds.

SUMMARY

Briefly, in accordance with the invention a full-spectrum luminaire is provided by the use of two types of fluorescent lamps one of which produces radiant energy, primarily in the visible range and the other produces radiant energy primarily in the near-ultraviolet range. The spectral energy distribution characteristics of each type of lamp is selected so that the combined output of both types of lamps has a spectral energy distribution characteristic approximately that of natural daylight. The mixing of the two types of radiation is done outside of a plurality of component lamps rather than inside of each lamp as in the prior art. This reduces replacement expense by permitting the UV component lamp, which degrades more rapidly, to be replaced separately from the other component lamps producing radiation in the visible range. A switching scheme is provided to enable the UV lamp to be switched off for desired intervals during which the energization of the other lamps in the luminaire may be continued to provide conventional illumination at night or any other desired time. The switching may be done manually or automatically by a timer to obtain the desired periodicity of the UV part of the luminaire radiation and this switching may be correlated with the time of day.

For a better understanding of the invention, reference should be made to the following detailed description taken in connection with the accompanying drawings.

DESCRIPTION OF ILLUSTRATED EMBODIMENTS

Figure 1:
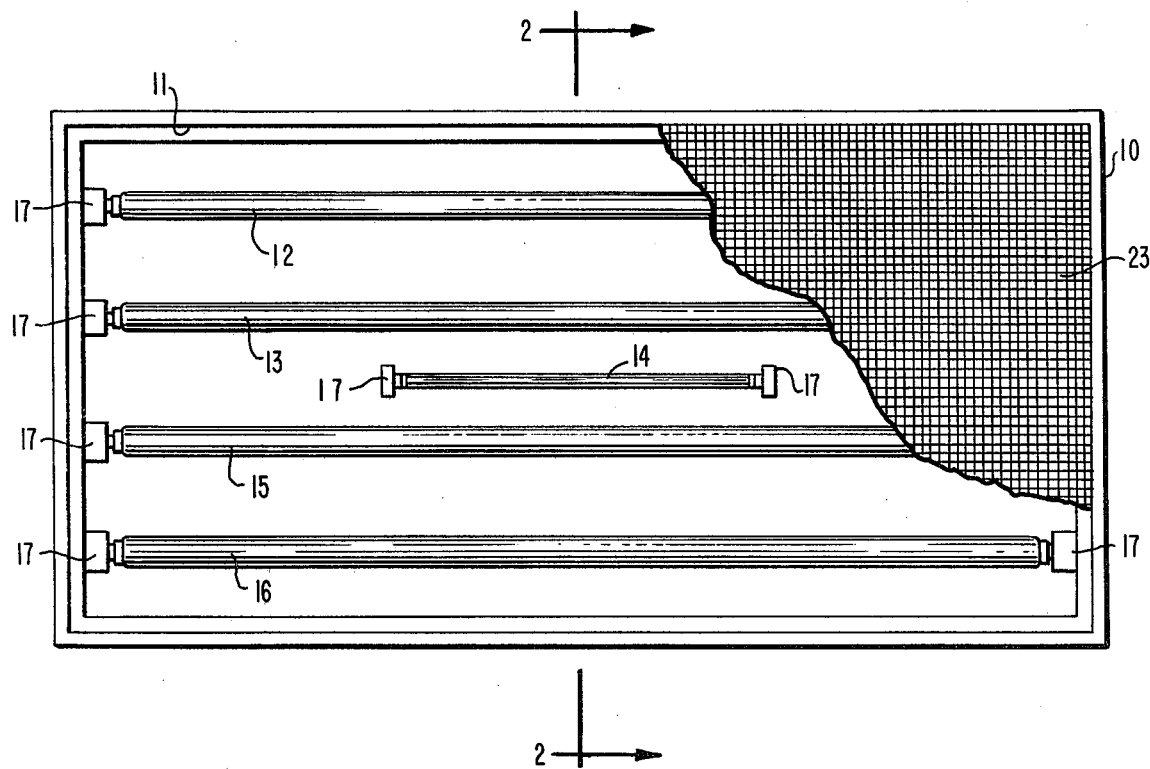
FIG. 1 is a bottom view of a luminaire embodying the present invention showing the arrangement of the component lamps.
Figure 2:
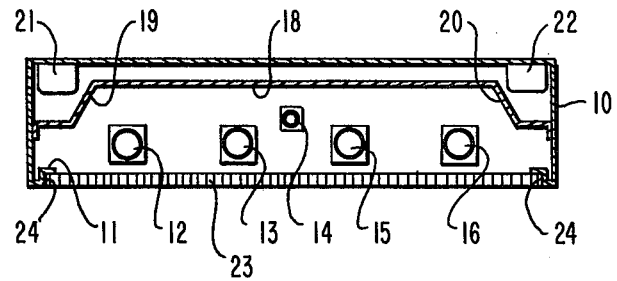
FIG. 2 is a sectional view of the luminaire shown in FIG. 1 taken along the section line 2—2 illustrating certain constructional details.

Referring to FIGS. 1 and 2 of the drawing there is shown a fluorescent lamp luminaire of the surface type suitable for mounting on a ceiling so as to illuminate an area below the luminaire. The luminaire comprises a rectangular housing 10 made of a suitable material such as aluminum fabricated so as to have an opening 11 facing downward through which light from the luminaire is projected. In the embodiment shown, the housing encloses five fluorescent lamps 12, 13, 14, 15, and 16 mounted to extend lengthwise of the housing in parallel, spaced relation. These lamps are of the bipin variety having electrode filaments adapted to be continuously heated during operation of the lamps. The contact pins at each end of the lamps are received and supported in conventional sockets 17 mounted on the ends of the housing 10 except for the lamp 14. This lamp, whose special characteristics are described below, has a lower wattage and is shorter than the other lamps. The sockets 17 for this lamp, which is centrally located, extend downwardly from the top of the housing and are supported in any suitable manner now shown.

In order to combine and reflect downwardly through opening 11 the light produced by the five lamps, there is provided a reflector 18 mounted above the lamps as shown. The reflector is formed of a material that reflects with reasonable efficiency both ultraviolet and visible light produced by the lamps. Preferably, the reflector is formed of aluminum with its surface adjacent the lamp highly polished for reflection efficiency. The side portions 19 and 20 of the reflector are slanted downwardly to provide the desired reflection angles and to provide mounting space in the housing for a power supply unit 21 and a stabilizer unit 22. These units are used to supply adequate starting and running voltages for the lamps and to regulate by ballasting or otherwise the operating current supplied to the lamps. Preferably, the lamps are supplied with cathode shields (not shown) of the type disclosed in U.S. Pat. No. 3,767,957.

To obtain desired shading and light diffusion the opening 11 is preferably covered by a suitable "egg crate" type of louver 23 supported by lips 24 extending inwardly from the housing 10 around the opening 11. In cases where shielding of RF radiation from the lamp is desired, a grounded screen of the type shown in U.S. Pat. No. 3,888,150 may be added.

According to the invention the luminaire utilizes first and second types of fluorescent lamps, the light outputs of which are mixed and combined outside of the tubes to form a composite radiation, the spectral energy distribution characteristic of which is approximately that of natural daylight in both the near (longwave) and visible wave bands. The first type used is a commercially available lamp which produces radiation primarily in the visible range i.e., 400 to 700 nanometers and has a spectral energy distribution characteristic in that range approximately that of natural daylight. Such lamps are often used for color matching purposes and one such lamp found satisfactory for the present invention is manufactured by General Electric Company and identified as "Chroma 50" fluorescent. The spectral energy characteristic of this lamp is shown in FIG. 6 and is identified as solid curve A.

Figure 6:
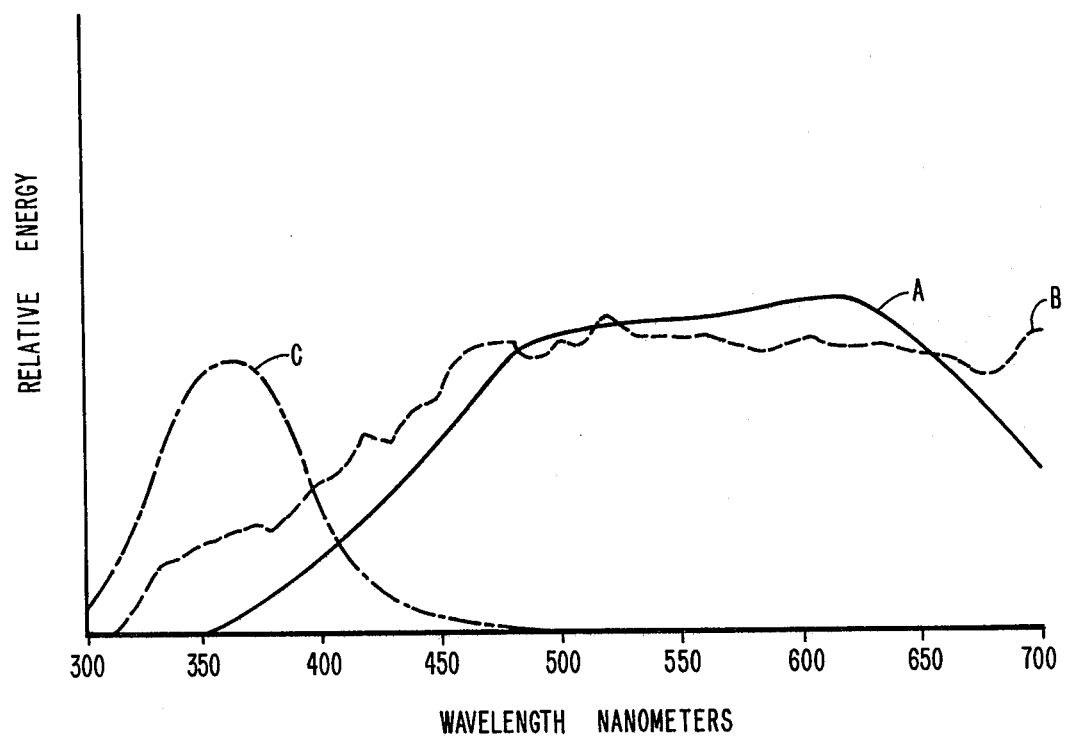
FIG. 6 is a graphical representation useful in explaining the theory and operation of the invention.

For the purpose of explanation and comparison FIG. 6 also shows as a dash curve "B" the spectral energy characteristic of natural daylight extending through the near ultraviolet and visible light wavelength band i.e., 320 to 700 nanometers. It will be noted that the lamp identified by curve A produces very little radiation in the short wavelength range of the near-ultraviolet and for that reason is not adequate by itself to act as a full-spectrum daylight lamp. To remedy this deficiency a second type of lamp is used which produces radiation primarily in the near-ultraviolet range. The spectral energy distribution of this second lamp is shown in FIG. 6 and identified by the dot-dash curve "C". The output characteristic of this lamp is chosen so that when its output is added to the output of one or more lamps having the characteristics of curve A the combined light output approximates that of natural daylight. One such lamp found suitable for this purpose is a commercially available so-called black light lamp manufactured by General Electric Company and identified by the number F15 T8/BL. This lamp was chosen because, as shown by curve C, it has in addition to UV output peaking at approximately 360 nanometers some overlapping output in the wavelength band of approximately 350 to 475 nonometers where the lamp identified by curve A is somewhat deficient. This can be seen by comparing curve A with natural daylight curve B. With reference to curves A and C it is noted that the mercury resonance peaks usually shown have been omitted for clarity the curves representing only the light output produced by phosphor conversion.

The matching of the two types of lamps to obtain the desired combined output approximating daylight involves a consideration of not only the spectral energy distribution curve but also the radiant power of the lamps as affected by their relative wattage. This can be done empirically and it has been determined one combination that produces the desired output resembling natural daylight in a luminaire of the type illustrated requires the use of four 40-watt lamps having the characteristic of curve A and one 15-watt black light lamp having the characteristic of curve C. The 40-watt lamps are identified by the numerals 12, 13, 15 and 16, while the black light lamp is identified by the numeral 14. As shown, the black light lamp 14 is centrally parallel and symmetrically disposed in the luminaire with respect to the larger lamps 12, 13, 15 and 16 to obtain optimum mixing of the two types of radiation.

If a luminaire of lower wattage is desired, the wattage of the two types of lamps may be reduced maintaining approximately the same output ratio. Thus, two rather than four 40-watt lamps of the curve A type may be used along with one black light lamp of the curve C type having approximately half the wattage such as an eight watt black light lamp manufactured by General Electric Company and identified by their numbers F8 T5-BL. Obviously other sizes may be designed using the same procedure.

Figure 3:
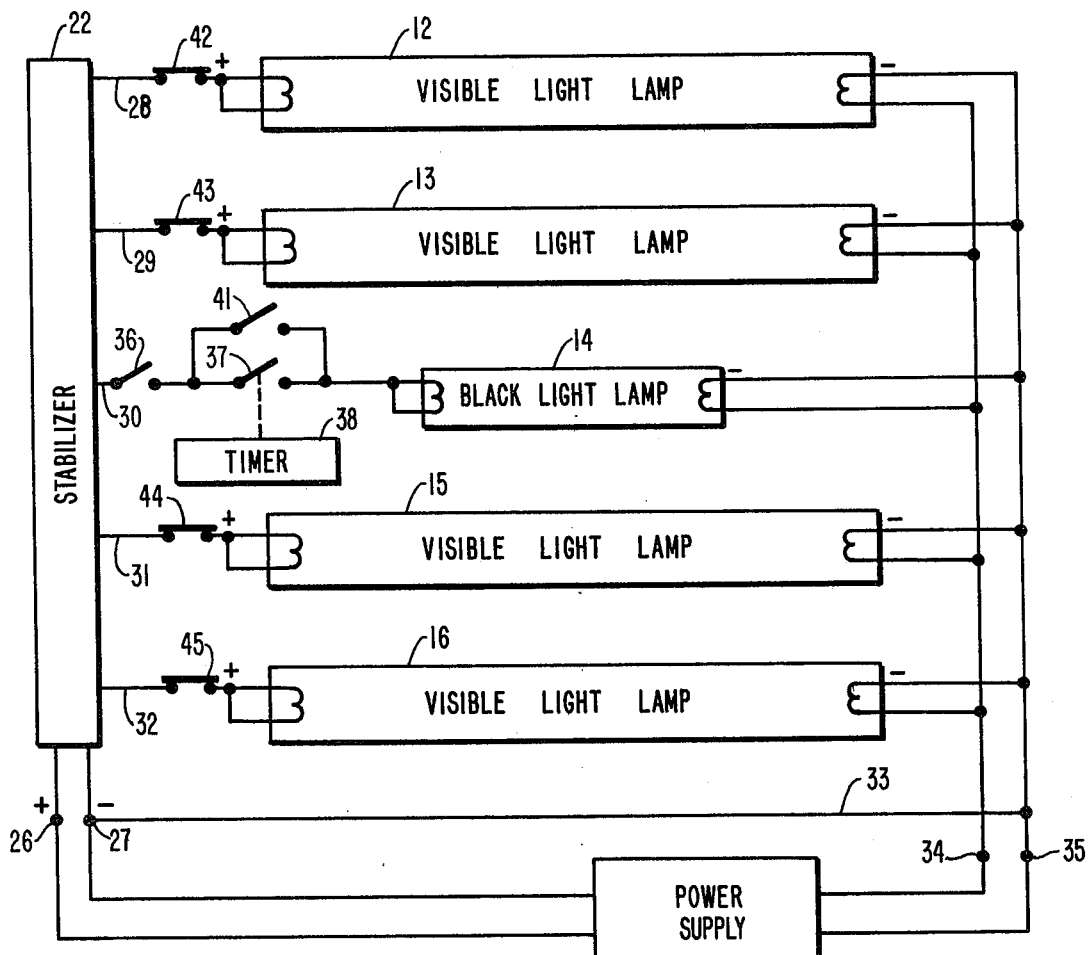
FIG. 3 is a schematic diagram showing how the component lamps are energized and switched to provide the desired lighting effects.

FIG. 3 of the drawing is a circuit diagram, partly schematic, illustrating how the lamps 12, 13, 14, 15 and 16 may be connected in parallel and the black light lamp 14 selectively disabled to alter the radiation output characteristic of the luminaire to obtain desired effects. The power supply 21 may be selected to provide either AC or DC operation of the lamp. Preferably, a DC system is used since it eliminates the 60 cycle flicker which may, in some cases, cause headaches, eyestrain, fatigue and other undesirable effects. The DC system has been chosen for illustration wherein the power supply unit 21 is energized from an AC power source to which it is connected by a master switch 25. The positive and negative DC output leads 26 and 27 are connected to the stabilizer 22 of known construction which supplies a regulated DC voltage of suitable starting and operating potential to the anodes of lamps 12, 13, 14, 15 and 16 through leads 28, 29, 30, 31 and 32, the negative return circuit from the cathodes being through common lead 33. The power supply also has output connections 34 and 35 from which heating current is conducted to the parallel conducted cathodes to heat the filaments. The stabilizer customarily has separate ballasting or current regulating devices for each of the lamps connected through the leads 28, 29, 30, 31 and 32 so that each lamp is separately energized and the current for each lamp separately regulated. With this arrangement it is possible to disconnect any of the lamps without affecting the operation of the remaining lamps.

A switch 36 in lead 30 is provided by means of which the black light lamp 14 may be selectively disabled to alter the radiation output characteristic of the luminaire. When switch 36 is open and lamp 14 disabled, the light output of the luminaire is primarily in the visible range which may be used for general illumination purposes. Such control action may be desirable to avoid possible overexposure to UV in cases where a luminaire having optimum UV output for short operating periods is operated continuously or for a period substantially longer than normal daylight hours. This can easily be accomplished in a luminaire embodying the present invention by merely opening switch 36.

Figure 4:
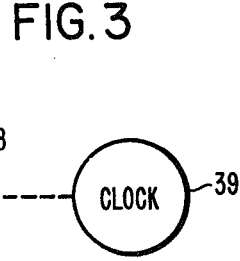
FIG. 4 shows a detail of the timer switch.
Figure 5:
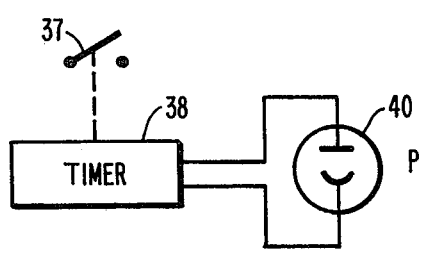
FIG. 5 illustrates an alternative arrangement of the timer.

In cases where circadian rhythms are involved or for research projects requiring biological studies of light, it may be desirable to control the periodicity of the UV light separately from the visible light. For this purpose there is provided an additional switch 37 in power lead 30 of lamp 14 actuated by a timer 38. The timer may be controlled by a clock mechanism 39 as in FIG. 4. The timer may also be controlled by a light-responsive device such as a photoelectric cell 40 responsive to sunlight and hence the time of day as in FIG. 5. An additional switch 41 bypassing the timer switch 37 may be closed when the timer is inactive to insure proper operation of the manual control switch 36.

For applications where special fluorescent lighting effects are desired additional switches in power leads 28, 29, 31 and 32 may be added to enable the black light 14 to be energized while one or more of the visible light lamps are deenergized. Normally closed switches 42, 43, 44 and 45 may be provided for this purpose and these switches may be ganged to operate them in any combination desired.

Because UV phosphors in fluorescent lamps degrade faster than phosphors producing visible light the operating life of lamps 12, 13, 15 and 16 is likely to be longer than that of black light lamp 14. An important cost advantage of the present invention is that the black light lamp 14 may be separately replaced at a low cost during the normal life of the visible light lamps. If all the lamps contained UV phosphors as in the prior art full-spectrum lamps, they would all have to be replaced when the UV phosphors degraded.

While there have been shown what are considered to be preferred embodiments of the invention, it will be apparent to those skilled in the art that various changes and modifications may be made in the lamp types and switching schemes used without departing from the spirit and scope of the invention.

What is claimed as new and desired to be secured by Letters Patent of the United States is:

1. A full-spectrum luminaire comprising:
   first and second types of gas discharge lamps arranged when energized to project the combined light produced by said lamps into an area to be illuminated the first type of lamp having a predetermined spectral energy distribution characteristic producing radiant energy primarily in the visible range and the second type of lamp having a predetermined spectral energy distribution characteristic producing radiant energy primarily, but not entirely, in the near ultraviolet range, with a peak output at approximately 360 nanometers, said second type of lamp having an output overlapping that of the first lamp in a wavelength band of approximately 350 to 475 nanometers whereby the combined light output of the lamps produced by the luminaire has a spectral energy distribution characteristic approximating that of natural daylight in both the near ultraviolet and visible ranges.

2. The luminaire of claim 1 including a housing having a light-emitting opening, the lamps being tubular and mounted within the housing in parallel spaced relation so as to project light uniformly through said opening into the area to be illuminated.

3. The luminaire of claim 2 including a reflector mounted within said housing and arranged to reflect the combined light from said lamps through said opening.

4. The luminaire of claim 3 wherein the reflector is formed of a material which reflects radiation in both the near-ultraviolet and visible wavelength bands.

5. The luminaire of claim 4 wherein the reflecting surface of the reflector is formed of polished aluminum.

* * * * *